United States Patent [19]

Vallee

[11] Patent Number: 5,062,300
[45] Date of Patent: Nov. 5, 1991

[54] DEVICE FOR THE ULTRASONIC NON-DESTRUCTIVE TESTING OF TUBES

[76] Inventor: Jean P. Vallee, 4, rue de la Fontaine, 78820 Juziers, France

[21] Appl. No.: 281,715

[22] Filed: Dec. 9, 1988

[30] Foreign Application Priority Data

Nov. 25, 1987 [FR] France ............................... 87 16353

[51] Int. Cl.⁵ ...................... G01N 29/06; G01N 29/26
[52] U.S. Cl. ........................................ 73/623; 73/628; 73/640; 73/641
[58] Field of Search .................. 73/623, 628, 641, 640, 73/642, 615

[56] References Cited

U.S. PATENT DOCUMENTS

| | | | |
|---|---|---|---|
| 3,810,384 | 5/1974 | Evans | 73/623 |
| 3,990,300 | 11/1976 | Kossoff | 73/640 |
| 4,008,603 | 2/1977 | Paulissen | 73/623 |
| 4,361,044 | 11/1982 | Kupperman et al. | 73/642 |
| 4,388,831 | 6/1983 | Sherman | 73/623 |
| 4,412,315 | 10/1983 | Flournoy | 73/623 |
| 4,437,332 | 3/1984 | Pittaro | 73/615 |
| 4,460,920 | 7/1984 | Weber et al. | 73/623 |
| 4,856,337 | 8/1989 | Metala et al. | 73/623 |

FOREIGN PATENT DOCUMENTS

| | | |
|---|---|---|
| 3131833 | 3/1983 | Fed. Rep. of Germany . |
| 0047757 | 4/1981 | Japan ................................. 73/628 |
| 59-44656 | 3/1984 | Japan . |
| 59-126946 | 7/1984 | Japan . |
| 61-31962 | 2/1986 | Japan . |
| 1075461 | 2/1964 | United Kingdom . |
| 2020023 | 11/1979 | United Kingdom . |

*Primary Examiner*—Hezron E. Williams
*Assistant Examiner*—Rose M. Finley
*Attorney, Agent, or Firm*—Larson & Taylor

[57] ABSTRACT

A ultrasonic device for non-destructive testing of thin tubes, for instance heat exchanger tubes, comprises a head having a longitudinal axis and insertable into a tube. A mechanism imparts to the head a rectilinear motion along and a rotational motion about the axis. The head contains ultrasonic transducers coupled with the tube through a fluid and able to transmit an ultrasonic beam in the form of volume waves in a direction at an angle with the longitudinal axis and to detect echoes. The transducers include one (or more) ultrasonic transducer delivering a focussed beam directed in a plane containing the longitudinal axis and at an angle with a direction perpendicular to the longitudinal axis, and one (or more) second ultrasonic transducer delivering a focussed beam parallel to a line perpendicular to the longitudinal axis and located at a distance from the line. Circumferential as well as longitudinal flaws may consequently be detected.

5 Claims, 4 Drawing Sheets

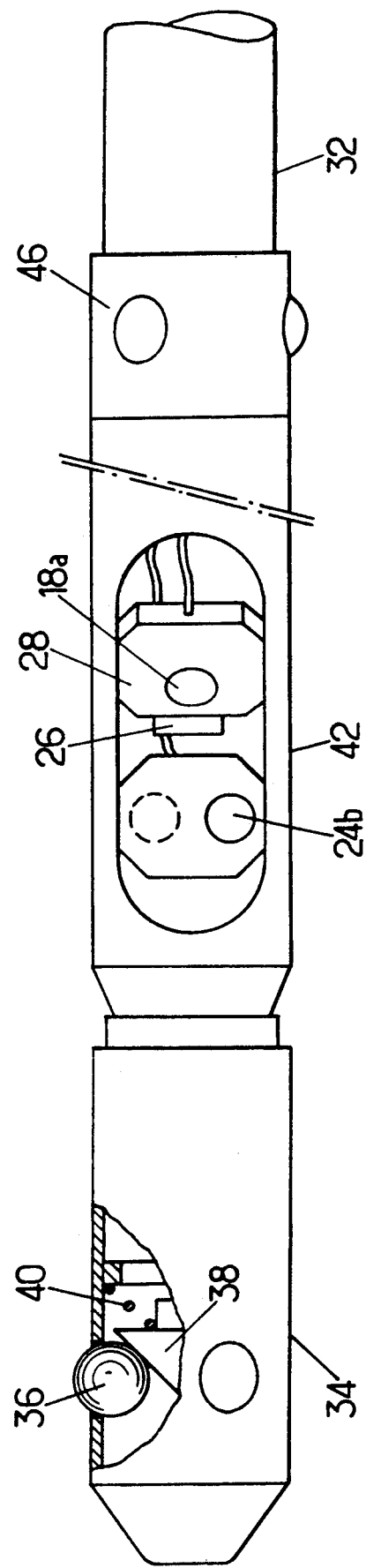

DEVICE FOR THE ULTRASONIC NON-DESTRUCTIVE TESTING OF TUBES

BACKGROUND OF THE INVENTION

1. Technical Field

The invention relates to an ultrasonic device for the non-destructive testing of thin tubes, of the type comprising a head insertable in the tube and having centering means in the tube and means for imparting to the head a rectilinear motion along a longitudinal axis and a rotational motion about the axis.

The invention is particularly suitable for use in the non-destructive ultrasonic testing of tubes in the steam generators of pressurized water nuclear power stations (PWRs).

2. Prior Art

Testing devices are already known in which a head is provided with means for centering it in the tube and rendering an axis of the head coincident with or parallel to the axis of the tube; the head contains ultrasound transducer means coupled with the wall of the tube by immersion in a fluid, and is able to transmit an ultrasonic beam and to detect echoes due to longitudinally oriented defects.

As compared with eddy current testing devices, devices using ultrasounds have an apparent drawback: the echo delivered by a fault or flaw, such as a crack, varies greatly with the orientation of the fault. If for example an ultrasonic transducer is used delivering a beam directed along a meridian plane of the tube, it is difficult to detect longitudinal cracks and the longitudinal sections of long cracks having an intricate shape.

SUMMARY OF THE INVENTION

It is an object of the invention to provide an improved ultrasonic testing device; more specifically, it is an object to provide a device able to detect not only faults oriented longitudinally with respect to the axis of the tube, but also faults having a circumferential development. For that, the transducer means comprise:

- at least one first ultrasonic transducer delivering a focussed beam directed in a meridian plane of the tube and at an angle with a direction perpendicular to the wall of the tube, and
- at least one second ultrasonic transducer delivering a focussed beam directed parallel to a diameter of the tube and located at a distance from said diameter so that the beam is oblique with respect to the wall of the tube.

Experience has shown that the detection of circumferential faults is not hindered by the presence of longitudinal faults and that the latter are reliably detected when the beam of the second transducer is refracted at an angle of about 45° in the wall, so as to detect faults by wedge effect. At the present time, there exists focused transducers, having a diameter as small as 6 mm, which may be placed sufficiently far away from the diameter with which they are parallel for fulfilling this condition in a heat exchange tube of the kind used in present day nuclear power stations.

The detection of transverse cracks is particularly difficult in those zones of the tube where the diameter varies, such as the ends of expanded zones, close to the tube plate. The change of the angle of incidence of the ultrasonic beam directed along zones of a meridian plane where the diameter varies, disturbs the measurement and may mask circular cracks. In a preferred embodiment of the invention, the difficulty is overcome by locating two first transducers symmetrically. Thus, when the variation of diameter disturbs detection in a given zone for one of the transducers, the other transducer directs the beam towards the zone through an undisturbed portion.

Two second transducers may also be disposed symmetrically, either for redundancy, or for increasing the detection speed, or for limiting the risk of nondetection of a crack masked by another crack, which is close to and parallel with the first one, in a particular detection direction.

When it is desired not only to detect cracks but also to identify the side of the wall into which they open, the length of the path followed in the thickness of the wall must be accurately determined. But a measurement of the flight time makes it possible only to determine the total path inside the tube and in the wall; any variation of distance between the transducer and the internal wall of the tube then disturbs the measurement.

To take these variations into account, there may be provided a head with an ultrasonic reflector placed in the immediate vicinity of the internal surface of the tube and located angularly to reflect a fraction of the beam reflected by the wall towards the transducer. The time of flight of the reflected beam is representative of the preliminary distance travelled through a coupling liquid and makes it possible to localize cracks without ambiguity.

Such correction or servo means have a high degree of precision since the same beam is used for detection and for correction. Experience has shown that a reflector having a very small diameter, typically having an area of about a square millimeter, is sufficient for obtaining a satisfactory echo. The reflector may also be used for monitoring acoustic coupling between the transducer and the wall of the tube and to discard the measurements when the degree of coupling is insufficient, for example if bubbles are interposed between the transducer and the wall.

The invention will be better understood from the following description of a particular embodiment, given by way of example. The description refers to the accompanying drawings.

BRIEF DESCRIPTION OF THE DRAWINGS

FIG. 8 shows a possible construction of the testing head.

DETAILED DESCRIPTION OF A PREFERRED EMBODIMENT

Figure 1:
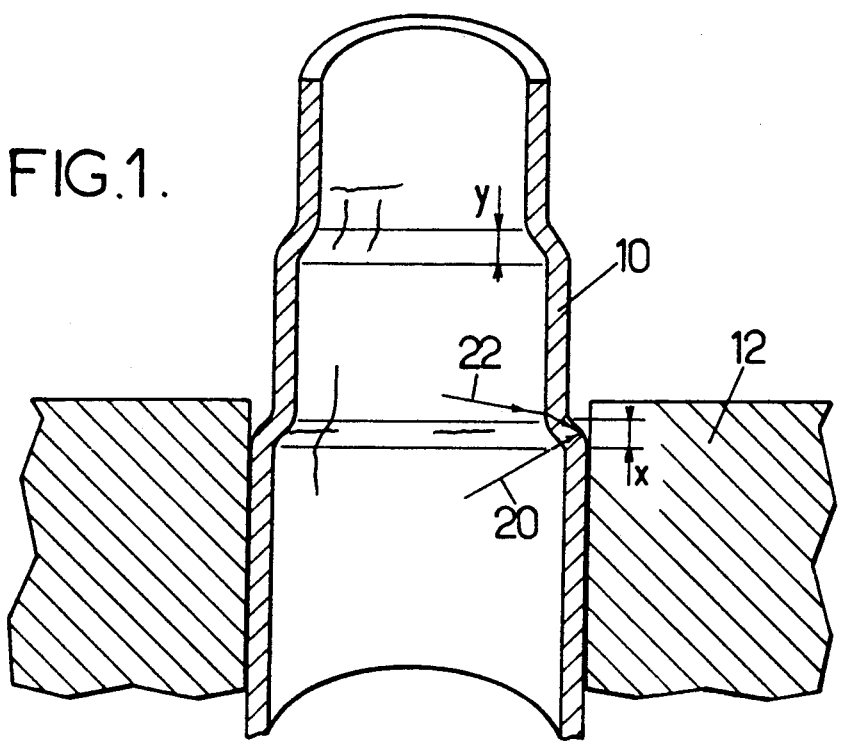
FIG. 1 shows schematically a section of a heat exchange tube, in a zone where the tube is fixed to a tube plate.

The general construction and a particular embodiment of a head for testing an exchanger tube of the kind shown schematically in FIG. 1 will be described by way of example. Referring to FIG. 1, a tube 10 is expanded in a tube plate 12 for securing it to the plate and has a zone of variable diameter, of length x, connecting the end of the expanded portion to the current portion of the tube. The tube may exhibit a second variation of diameter in a zone of length y if a diametral deformation of the intermediate zone has been provided for lowering the tensile stresses.

The steam generator tubes are generally made from a chromium-nickel-iron alloy known as "INCONEL 600". In such tubes intergranular cracks may appear, due to stress corrosion, particularly in the end portions of the expanded zones. Most of the cracks which appear are longitudinal. Their evolution in time is well known and there is no danger that they give rise to catastrophic failures. But transverse cracks may also appear. They expand very rapidly and, when they are detected, the corresponding tubes must be plugged as a preventive measure.

It is consequently important that the testing device be able to determine not only the existence of flaws, but also their angular position.

Figure 2:
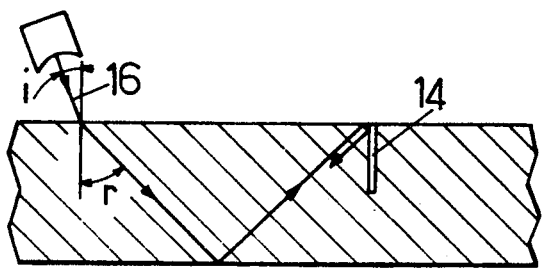
FIGS. 2 and 3 show diagrammatically the path followed by a ultrasonic beam directed in a meridian plane at an angle selected for detecting circumferential cracks opening into the internal wall (FIG. 2) or external wall (FIG. 3) by wedge effect, FIG. 4, similar to FIG. 3, shows the detection of longitudinal cracks using a beam directed parallel to a diameter.
Figure 3:
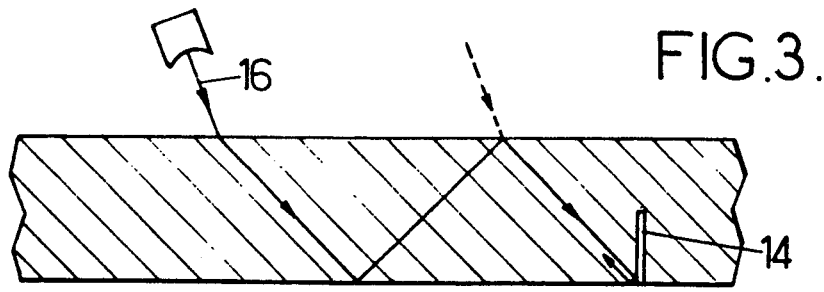

In the device which will be described, there is used at least one transducer delivering a focussed beam whose angle of incidence is such that the beam is at a 45° angle with respect to the perpendicular inside the wall of the tube for detecting longitudinally oriented faults. The fault formed by an internal crack 14 will then be detected due to the reflection of beam 16 in the angle formed by the fault and the internal surface (FIG. 2) or external surface (FIG. 3) of the tube wall. A focussed, i.e. convergent beam is advantageously used; it is delivered in volume wave mode. Miniature transducers are already known whose diameter may be as low as about 6 mm, for delivering a convergent beam. Detection may take place, in the case of an internal fault, with a single rebound (forth and back path) of the beam on the external face, or with two rebounds or even more. In practice, it will often be preferable to eliminate the detections corresponding to two rebounds of the beam or more, for which the attenuation is high; a timing gate may be used for selection of the appropriate echoes.

Detection of an external fault (FIG. 3), may for example take place for a half-rebound and one rebound and a half. The position of the crack may be derived from the outward-inward time of flight of the beam.

In general, it will be desirable to use a transverse-wave mode because a longitudinal wave mode is always accompanied by a transverse wave (due to its higher velocity) which may generate an ambiguity as to the position of the detected fault. In addition, the limit resolution is better with a transverse wave, whose wavelength is almost half that of the longitudinal wave.

This will lead to adoption of an angle of incidence i of about 20° to obtain a refraction angle r=45° in a material such as "INCONEL".

Figure 4:
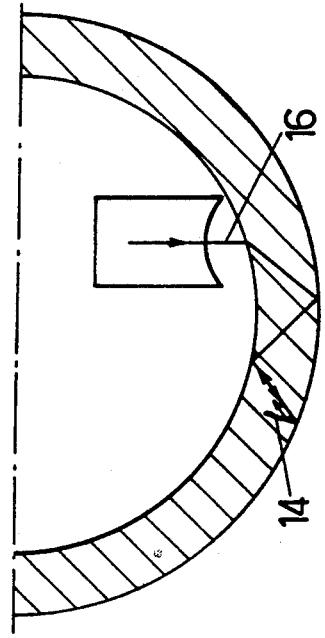

The indications given above concerning the transducers for detecting transverse faults are also valid when detecting longitudinal faults where the requirement of an angle of incidence of about 20° will require a specific distance between the axes of the transducers and a same diametral line, at least when the axes of the transducers are parallel to the same diameter (FIG. 4).

As mentioned above, the use of a single transducer for detecting transverse faults may leave cracks unnoticed if they are masked by a variation in the diameter. To overcome the difficulty, two transducers 18a and 18b are disposed, symmetrically with respect to transverse cracks. It is of advantage to stagger the transducers with respect to each other so that they probe complementary zones, separated by half a step of rectilinear advance. Thus, possible deviations in the angle of incidence and the shadow effect caused by a crack which may mask a parallel and near-by crack are partially overcome. The transducers may also be positioned so that they examine zones which are mutually offset in the longitudinal direction by half a step of advance, when the testing head is helically moved. An offset of 0.5 mm may for example be used using a helical advancing step of 1 mm per revolution, for reducing the time required for testing.

An essential advantage in using two transducers in mutually opposed position is the fact that the dead zones due to diameter variations disappear. Referring to FIG. 1, the bean 20 arriving from the direction shown will not allow detection, due to its incorrect incidence, but on the other hand beam 22 will make detection possible.

The other two transducers 24a and 24b of the head are for detecting longitudinally oriented faults. They are mounted in mutually parallel opposition (FIG. 6), i.e. they deliver parallel beams. Their offset along the longitudinal axis will again be advantageously an odd multiple of the half step of advance.

It may be determined whether a fault opens into the internal surface or the external surface of the tube wall by comparing the outward-inward time of an ultrasonic pulse with predetermined values. Such determination may be made using time measurement gates corresponding to the time of flight for one rebound and one-and-a-half-rebound echo. But these two echoes are only separated by a very short time t:

$$t = e\sqrt{2}/V_t$$

where e is the thickness of the tube (in the 1 mm range of magnitude in the case of an exchange tube). If the tube is of INCONEL, $V_t = 3020$ m.s$^{-1}$ which corresponds to a travel time $t = 0.42$ μs.

Considering the shortness of time t, any error concerning the duration of the preliminary travel time a (FIG. 7) may cause an error of interpretation. Now, the inner diameter of the tube is only defined with some tolerance and centering of the head may not be perfect.

To overcome the difficulty, a time reference used for the selection gates is not the transmission time of an ultrasonic pulse, but the reception time of a readily identifiable echo whose time of appearance has the same law of variation with respect to the preliminary travel time a as the flight time.

Since the angle of incidence i is high, the energy reflected toward the transducer by the tube wall may be insufficient to provide a reference echo and there is no sufficient space available to use a second transducer for providing a time reference.

Figure 7:
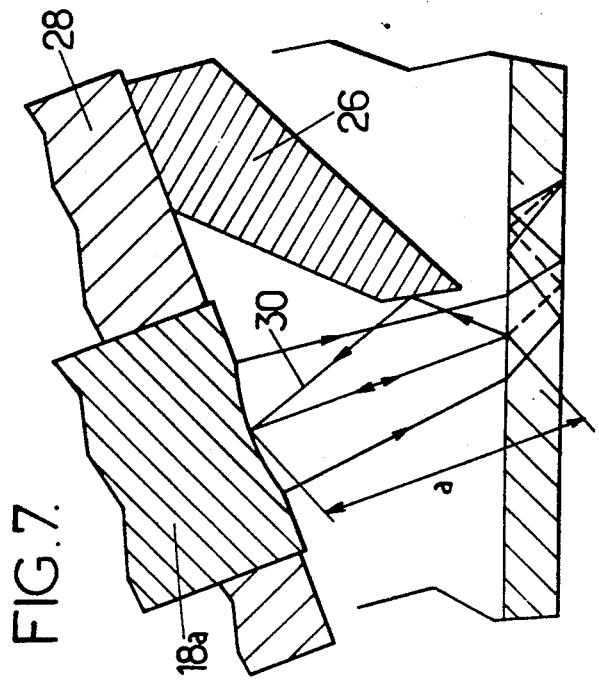
FIG. 7 shows a reflector fitted to the support of a transducer for measuring the preliminary path.

As shown in FIG. 7, a reference echo is delivered by a reflector 26 fixed to the corresponding transducer, 18a for example. Transducer 18a and reflector 26 are fixed to the common support 28 which holds the reflector in an angular position such that the amount of energy reflected by the internal surface of the tube wall reaches back to the transducer. With this arrangement, the angle of the reflected beam 30 used for the servo-control by adjusting the time gates is the same as that of the angle of the main beam and makes the preliminary travel time correction accurate, all the more since the point of impact on the internal surface of the wall is the same for the detection beam and for the servo-control beam. Correction takes place then exactly at the position of the measurement.

Figure 5:
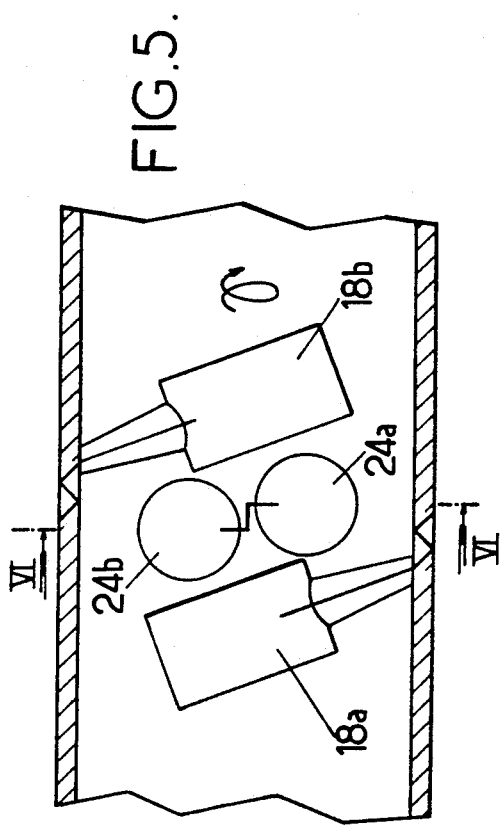
FIGS. 5 and 6 show, respectively in cross-section through a longitudinal plane and in cross-section along plane VI—VI of FIG. 5, a possible distribution of four transducers in a testing head.
Figure 6:
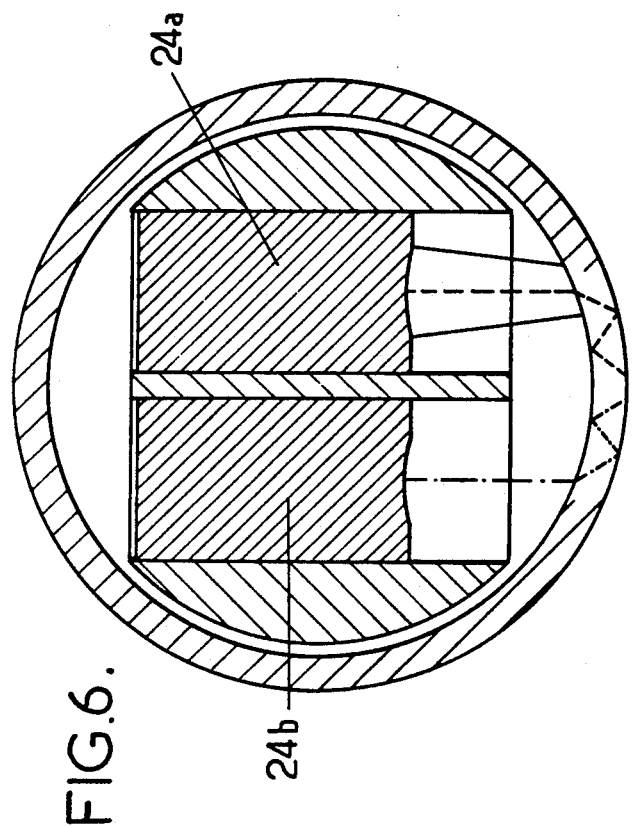

FIG. 8 shows a possible construction of a measuring head using a transducer arrangement of the kind shown in FIGS. 5 and 6. The head is fixed to the end of a flexible tube 32 for moving it along an exchanger tube and for defining a passage for electric connections with the transducers. The head is in several mutually connected parts. It is provided with an end piece 34 having a tapered tip for easier insertion thereof into the tube and having a centering device. Great accuracy is not required from such a device since possible deviations may be compensated with the use of the reflector. As shown the centering device is formed of three balls 36 which a pusher 38, subjected to the pressure of a spring 40, biases toward the predetermined outmost position shown in FIG. 8. It could be replaced with a simpler device, for example flexible brushes: its essential purpose is to maintain the angle of incidence within acceptable limits.

The active part of the head is formed as a tube section 42 having a window, of elongate shape in the axial direction, which receives the transducers. Each transducer is mounted in a support, such as the parallelepipedic shaped support 28 of FIG. 8.

The active part is connected to a sleeve 46 having a centering device which may be identical to that of end piece 34. The wires for connection between the transducers and remote electronics are placed in the flexible tube.

By way of example, satisfactory results have been obtained on heat exchanger tubes using focussed transducers operating at a frequency of 10 MHz, having a diameter of 6 mm, with an angle of incidence of 20°. For tubes with that diameter, it is even preferable to work at a higher frequency, for example 15 or 20 MHz, which seems best to compromise between attempts to have a minimum diameter, focusing, an acceptable advance step and a distance a (FIG. 7) of the transducers compatible with the internal diameter of the tube.

In the case of the exchange tubes already mentioned, a distance of 3.5 mm between the axes of each transducer 24a, 24b and the diameter of the tube parallel to the axes makes it possible to attain an optimum incidence of 20° and has given good results.

Figure 9:
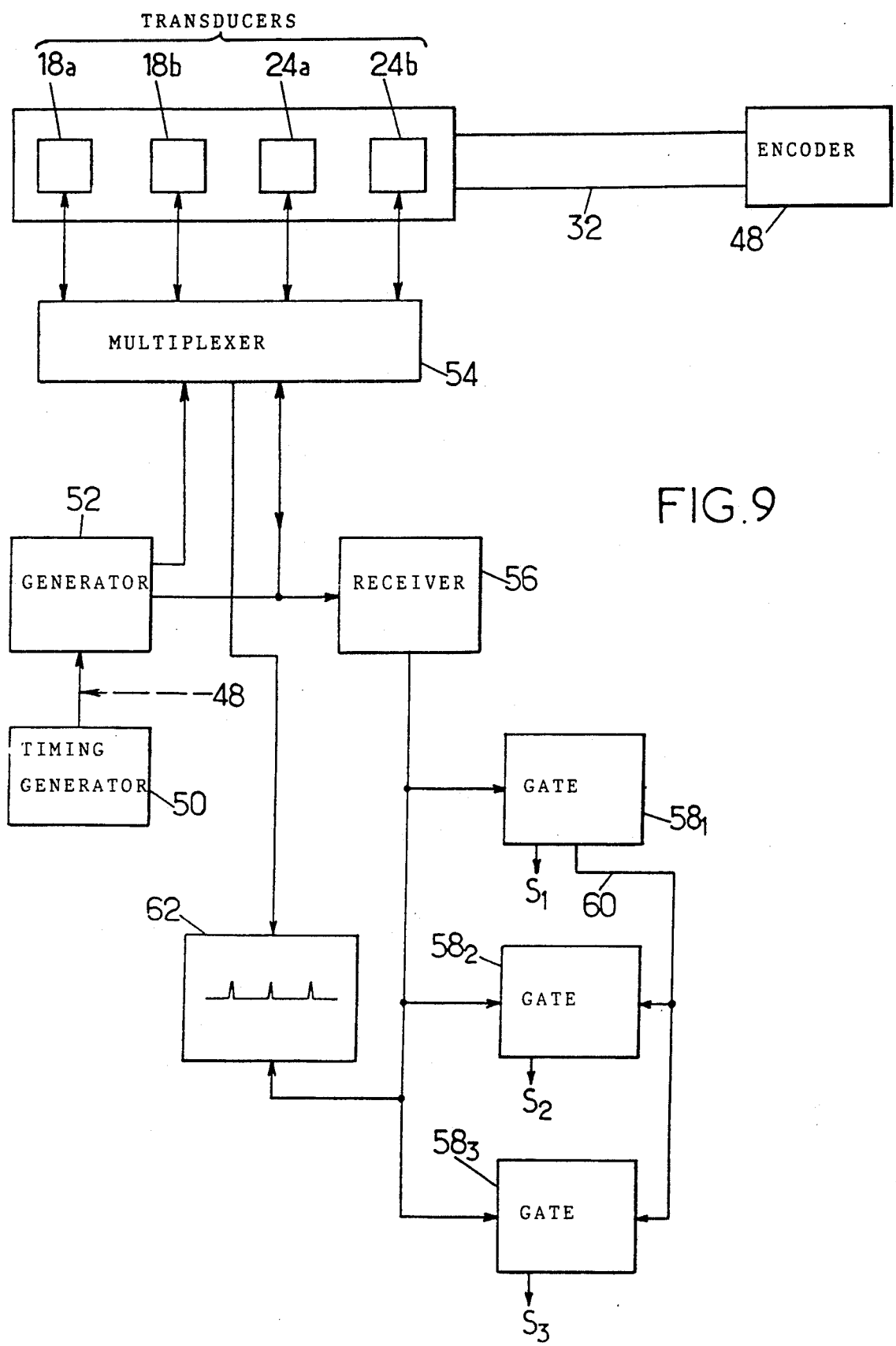
FIG. 9 is a general block diagram of circuits associated with the head of FIG. 8.

Referring to FIG. 9, there is illustrated a block diagram of a circuit suitable for use with the head, for C-scan echography and for use of the echoes by a processing computer (not shown) whose construction may be conventional. The head is fixed to the end of tube 32 carried by a drive mechanism which imparts a helical movement to the head. The mechanism is provided with conventional means for measuring the angular position and the axial position of the head, connected to the processing unit.

The circuit comprises a timing generator 50 for repetitively triggering the detection sequence. The rate is chosen as a function of the advancing speed of the head. This generator may be an angular encoder 48 controlled by the rotation of the probe head so that the measurements are independent of the movement defects of the head. Generator 50, possibly 48, controls a generator 52 delivering electric pulses for energizing the transducers and a synchronization signal at a frequency four times lower. A multiplexer 54 connects the four transducers 18a, 18b, 24a, 24b successively to the pulse generator. The pulse energizing a transducer and the associated echoes are received by receiver 56, comprising amplifying, rectifying and filtering circuits, whose output is connected to three analog gates $58_1$, $58_2$ and $58_3$. Gate $58_1$ is connected for passing the reflected servo-control echo to a synchronization output 60. For that, it is enabled after a fixed time delay from delivery of a pulse by generator 52, through a delay element (not shown). The other two gates $58_2$ and $58_3$ are enabled with different delays with respect to the synchronization and servosignal. The time delays and opening times of the gates are such that they respectively isolate echoes from "internal" and "external" flaws. The outputs $S_1$, $S_2$ and $S_3$ of the three gates are connected to the processing unit.

For A-scan echography, the pulsed signal delivered by the multiplexer for selecting a transducer among the four transducers is applied to the sweep triggering input of an oscilloscope 62 which receives the output signal from receiver 56. The reflected servo-echo, the possible flaw echo and a background echo appear on a CRT display.

In this embodiment, due to the presence of the multiplexer, the number of elements in the ultrasonic system is limited. For convenience, it may be possible to construct the system with four single channel ultrasound units.

We claim:

1. Ultrasonic device for non-destructive testing of tubes having a thickness which is small as compared with their diameter, comprising a head having a longitudinal axis and insertable into a tube along said longitudinal axis means for centering the head in a tube and means for imparting to the head a rectilinear motion along said longitudinal axis and a rotational motion about said axis, said head containing ultrasonic transducer means arranged to be coupled with a wall of a tube into which said head is introduced through a fluid and able to transmit an ultrasonic beam in a direction at an angle with said longitudinal axis and to detect echoes of said beam, wherein said transducer means comprise two first ultrasonic transducers located symmetrically with respect to a plane perpendicular to said axis and delivering a focussed base directed in a plane containing said longitudinal axis and at an angle with a direction perpendicular to the longitudinal axis, and two second ultrasonic transducers located symmetrically with respect to a plane perpendicular to said longitudinal axis and each delivering a focussed beam directed parallel to a line perpendicular to said longitudinal axis and located at a distance from said line whereby the beam is oblique with respect to the wall of a tube into which said head is introduced.

2. Device according to claim 1, wherein said two second ultrasonic transducers are offset along said axis by one half the distance over which said head is moved rectilinearly per turn of said rotational motion during said rectilinear motion.

3. Device according to claim 1, wherein said first and second ultrasonic transducers are so angularly located that the angle of the beam delivered by each one of said transducers in a tube wall is about 45° with respect to a line orthogonal to a tube wall.

4. Device according to claim 1, wherein said means for centering said head in said tube comprises a plurality of balls retained in said head, distributed at angular intervals about said longitudinal axis and by resilient pushing means biasing said balls in a direction radially outwardly of said head.

5. Ultrasonic device for non-destructive testing of tubes having a small thickness as compared with their diameter, comprising a head having a longitudinal axis and insertable into a tube along said longitudinal axis, means for centering the head in a tube and means for imparting to the head a rectilinear motion along said longitudinal axis and a rotational motion abut said axis, said head containing ultrasonic transducer means arranged to be coupled with a wall of a tube into which said head is introduced through a fluid and able to transmit an ultrasonic beam in the form of a volume waves in a direction at an angle with said longitudinal axis and to detect echoes of said beam, wherein said transducer means comprise at least one first ultrasonic transducer delivering a focussed beam directed in a plane containing said longitudinal axis and at an angle with a direction perpendicular to the longitudinal axis, and at least one second ultrasonic transducer delivering a focussed beam directed parallel to a line perpendicular to said longitudinal axis and located at a distance from said line whereby the beam is oblique with respect to the wall of a tube into which said head is introduced, wherein one at least of said first and second ultrasonic transducers is provided with a reflector for receiving an echo of said beam on an internal face of a tube wall and reflecting said echo toward the respective transducer, and wherein said head is operatively associated with a circuit having range gates for separating echoes due to internal faults and external faults in a tube into which said head is introduced, said gates being synchronized by a signal generated responsive to the echo from said reflector.

* * * * *